United States Patent
Pekkan et al.

(10) Patent No.: US 10,729,529 B2
(45) Date of Patent: Aug. 4, 2020

(54) SYSTEM FOR PRE-OPERATIVE DEVELOPMENT OF PATIENT-SPECIFIC VASCULAR PATCH GRAFT PROTOTYPES FOR PEDIATRIC AND NEONATAL PATIENTS

(71) Applicant: Koc Universitesi, Sariyer, Istanbul (TR)

(72) Inventors: Kerem Pekkan, Istanbul (TR); Senol Piskin, Istanbul (TR)

(73) Assignee: Koc Universitesi, Sariyer, Istanbul (TR)

( * ) Notice: Subject to any disclaimer, the term of this patent is extended or adjusted under 35 U.S.C. 154(b) by 438 days.

(21) Appl. No.: 15/824,845

(22) Filed: Nov. 28, 2017

(65) Prior Publication Data
US 2018/0078356 A1 Mar. 22, 2018

Related U.S. Application Data (63) Continuation of application No. PCT/TR2015/000243, filed on May 29, 2015.

(51) Int. Cl.
*A61F 2/06* (2013.01)
*G06T 17/00* (2006.01)
*A61F 2/24* (2006.01)

(52) U.S. Cl.
CPC ............ *A61F 2/06* (2013.01); *G06T 17/00* (2013.01); *A61F 2/2415* (2013.01); *A61F 2240/002* (2013.01); *A61F 2250/0082* (2013.01); *G06T 2210/41* (2013.01)

(58) Field of Classification Search
CPC ........ A61F 2240/002; A61F 2250/0082; A61F 2/06; A61F 2/2415; G06T 17/00; G06T 2210/41; G06T 17/20; G06T 17/205
See application file for complete search history.

(56) References Cited

PUBLICATIONS

Kelvin KL Wong et al., "Hemodynamic analysis of virtual stent design for atherosclerotic carotid artery", 2011 Computing in Cardiology (CINC 2011); Hangzhou China, Sep. 18-21, 2011, IEEE, Piscataway, NJ, Sep. 18, 2011 pp. 157-160, XP032126898, ISBN: 978-1-4577-0612-7. (Year: 2011).*

Imani M et al., "The comprehensive finite element model for stenting: The influence of stent design on the outcome after coronary stent placement", Journal of Theoretical and Applied Mechanics Warsaw University of Technology Poland, vol. 51, No. 3,2013, pp. 639-648, ISSN: 1429-2955; Nov. 14, 2012. (Year: 2013).*

Kerem Pekkan et al., "Patient-specific surgical planning and hemodynamic computational fluid dynamics optimization through free-form haptic anatomy editing tool (SURGEM)," Jan. 23, 2007, Med Biol Eng Comput, DOI 10.1007/s11517-008-0377-0, pp. 1-14.

(Continued)

*Primary Examiner* — Alexander M Weddle
(74) *Attorney, Agent, or Firm* — Brinks Gilson & Lione (57) ABSTRACT

The present disclosure relates to a system for manufacturing of vascular patches in the form pre-operative surgical planning prototypes providing optimized patient specific 3-D patch geometries. The present disclosure relates more particularly to a patch generation device for manufacturing of vascular patches in the form pre-operative surgical planning prototypes providing optimized patient-specific patch geometries, said patch generation device comprising a processing unit effectuating processing of the optimized patient-specific patch geometries.

15 Claims, 3 Drawing Sheets

(56) References Cited

PUBLICATIONS

Salvatore Pasta et al., "Computer modeling for the prediction of thoracic aortic stent graft collapse," Basic Research Studies, Eastern Vascular Society, Apr. 24, 2012, Journal of Vascular Surgery vol. 57, No. 5. pp. 1-9.

International Search Report, dated Feb. 29, 2016, pp. 1-2, issued in International Application No. PCT/TR2015/000243, European Patent Office, Berlin, Germany.

Kelvin KL Wong et al., "Hemodynamic analysis of virtual stent design for atherosclerotic carotid artery", 2011 Computing in Cardiology (CINC 2011); Hangzhou China, Sep. 18-21, 2011, IEEE, Piscataway, NJ, Sep. 18, 2011 pp. 157-160, XP032126898, ISBN: 978-1-4577-0612-7.

Imani M et al., "The comprehensive finite element model for stenting: The influence of stent design on the outcome after coronary stent placement", Journal of Theoretical and Applied Mechanics Warsaw University of Technology Poland, vol. 51, No. 3, 2013, pp. 639-648, ISSN: 1429-2955; Nov. 14, 2012.

International Preliminary Report on Patentability, dated Jul. 31, 2017, pp. 1-6, issued in International Application No. PCT/TR2015/000243, European Patent Office, Berlin, Germany.

* cited by examiner

SYSTEM FOR PRE-OPERATIVE DEVELOPMENT OF PATIENT-SPECIFIC VASCULAR PATCH GRAFT PROTOTYPES FOR PEDIATRIC AND NEONATAL PATIENTS

PRIORITY

This application is a continuation of International Patent Application No. PCT/TR2015/000243 filed May 29, 2015, which is herein incorporated by reference in its entirety.

TECHNICAL FIELD

The present disclosure relates to a system for manufacturing of vascular patches in the form pre-operative surgical planning prototypes providing optimized patient specific 3-D patch geometries.

BACKGROUND

The work leading to this disclosure has received funding from the European Research Council Proof of Concept Grant under the European Union's H2020, ERC grant agreement number 641156.

Congenital cardiovascular defects in neonatal and pediatric patients are treated through palliative reconstructive surgical operations where the commercially available vascular transplants/grafts are generally fabricated from synthetic "non-remodeling" materials. Compared to adults, cardiovascular structures of neonatal and pediatric patients grow in size and their vascular micro-structure alters significantly with aging under increasing mechanical loads.

Typically, a series of open-heart surgeries must be performed at progressive stages of growth (First stage at birth, second stage in 2-3 years old, third stage in 4-5 years old and further operations in adulthood (~50 years+)) since artificial grafts are unable to comply with changing vascular size and fail beyond their operating dimensions unlike live tissue. Additionally, it is further to be noted that surgical grafts should have geometries specifically engineered to the specific patient as cardiovascular anatomies are highly complex and differ between patients.

Treatment of cardiovascular defects in neonatal and pediatric patients therefore involves significant complexity and is prone to serious medical complications compared to adult patients. Due to the nature of the cardiovascular structures of neonatal and pediatric patients and their vascular micro-structure altering with aging under increasing mechanical loads, surgical operations are successively conducted by which the commercially available vascular patches are implanted to the patient. However, as noted, since the cardiovascular anatomies have complex differentiating structures, commercially available square or rectangular two dimensional patches are typically needed to be structured and shaped prior to the operation by the surgeon according to the specific needs of the patient.

SUMMARY

The primary disadvantage associated with the above procedure lies in that the determination of the physical characteristics and the optimum geometrical shape of the patch including the stitching line's length and geometry is correlated with the experience of the surgeon. Standard artificial patch materials in rectangular form are needed to be cut in appropriate sizes according to the specific needs of the patient Inappropriately configured patches not only cause loss of patch material but may typically lead to undesired graft deformations such as wrinkling in the case of patches larger than required and vascular stenosis if a patch smaller than necessary is implanted. If it turns out that the implanted patch was not tailored to the individual patient's anatomy, the surgeon further intervenes to recruit neighboring tissue to solve the problem, which may in turn cause excessive or unnecessary stress on the stitches and uncontrolled growth of the local tissue. Further, wrinkling on the graft causes early stage deformations due to the deviation of the hemodynamic forces on the vascular cells from the physiological values.

While excessive stitching imposes unnecessary loads on the graft, it is to be noted that optimization of the stitching line in an appropriately structured patch removes the possibility of excessive stitching.

It is further to be noted that patch grafts without an accurately modeled 3-D design leads to distorted vascular architecture consuming extra energy from the heart. As a final critical inconvenience, the time period the surgeon needs during the surgery in order for preparing and designing the artificial patch may critically increase the coronary bypass surgery duration, which may than result with brain and systemic tissue damage, in which case especially neonatal and pediatric patients' brain development can be affected dramatically.

A prior art publication in the technical field may be referred to as WO/2013/019756, which discloses artificial heart valve structures and methods of their fabrication. The heart valve structures may be fabricated from a biocompatible polymer and include one or more heart valve leaflet structures incorporated within a conduit. The valve structures may incorporate one or more conduit sinuses, as well as a gap between the lower margin of the valve leaflets and the interior of the conduit. In addition, the valve structures may include one or more valve sinuses created in a space between the valve leaflets and the conduit inner surface. Computational fluid dynamics and mechanical modeling may be used to design the valve leaflets with optimal characteristics. A heart valve structure may also incorporate a biodegradable component to which cells may adhere The incorporated cells may arise from patient cells migrating to the biodegradable component, or the component may be pre-seeded with cells prior to implantation in a patient.

The present system provides a computer aided pre-operative surgical planning device for optimization of patient specific 3D graft geometries to serve as a reference to the operator.

The present system is devised under the recognition that it remains a need that grafts being implanted should have a longer service life. Patient specific 3D graft geometries serving as a reference to the surgeon will eliminate undesired graft deformation such as wrinkling and enable optimization of stitching to remove the possibility of excessive stitching that impose unnecessary stress on the graft.

An interesting feature of the system is to provide a patch generation device for the development of patient specific 3D graft geometries to be used as pre-operative reference prototypes.

Congenital heart defects relates to defects in the structure of the heart that are present at birth. The blood flow is affected by the defects in the heart's vascular structure. The treatment of cardiovascular defects depending on the type and severity of the defect requires palliative reconstructive surgical operations where vascular patch grafts are implanted to the patient.

According to the present disclosure, a system includes a patch generation device in the form of a computer aided pre-operative planning station generates patient specific vascular graft prototypes. The prototypes serve for the purpose of avoiding undesired graft deformations on the cardiovascular vessels of the patient by serving as 3D graft models in the form of reference structures to guide the operator in designing the artificial patch graft to be implanted. Therefore, the surgeon will be able to detect graft positions that may lead to undesired graft deformation such as wrinkling or to optimize stitching to remove the possibility of excessive stitching that impose unnecessary loads on the graft.

The disclosure therefore relates to a system that includes a device to produce 3D patient specific vascular graft structures by a 3D graft planning system. The system includes memory and a processor with circuitry that is executable to run a plurality of specifically dedicated software modules in communication with a prototype module executed by the processor to effectuate 3D production of the patch grafts.

BRIEF DESCRIPTION OF THE FIGURES

Accompanying drawings are given solely for the purpose of exemplifying system that includes a patch generation device for developing patient specific 3D graft geometries, whose advantages over prior art were outlined above and will be explained in brief hereinafter.

The drawings are not meant to delimit the scope of protection as identified in the claims nor should they be referred to alone in an effort to interpret the scope identified in said claims without recourse to the technical disclosure in the description.

DETAILED DESCRIPTION

Figure 1:
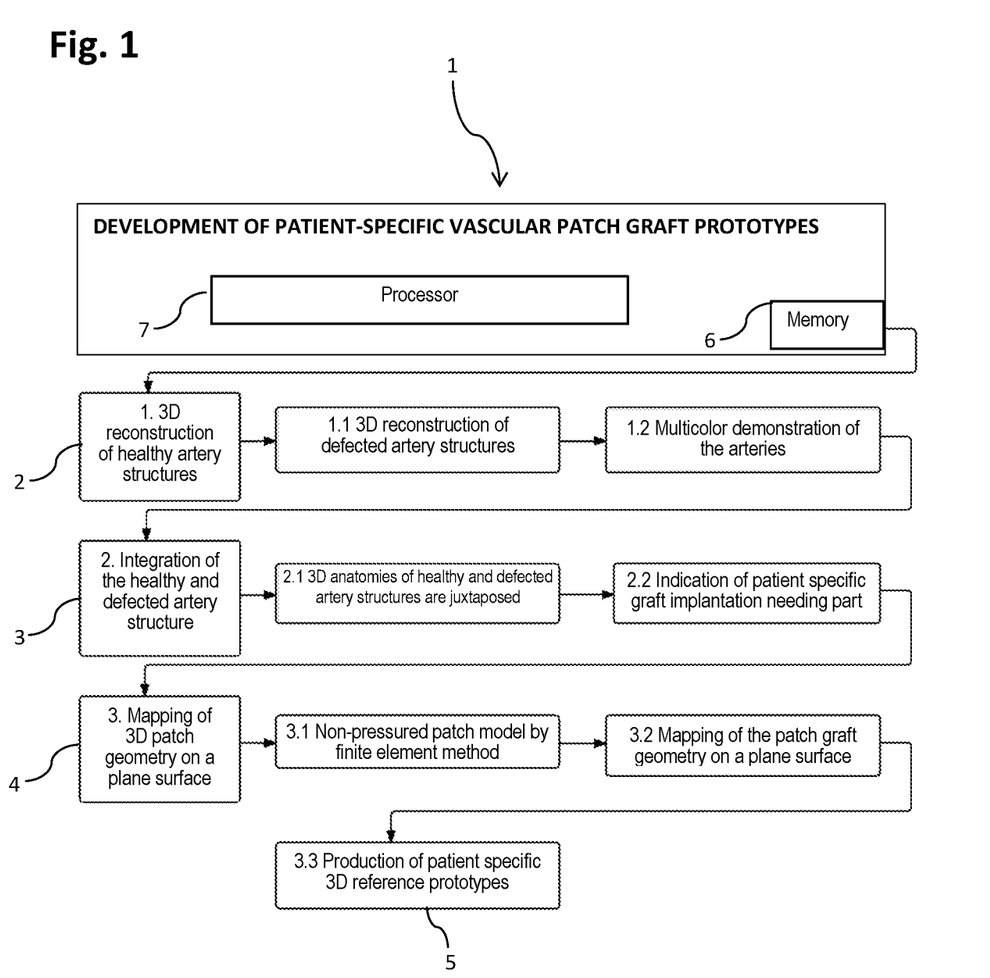
FIG. 1 demonstrates operational steps of a system that includes a pre-operative patch generation device for the fabrication of grafts patches having patient-specific geometries.
Figure 2:
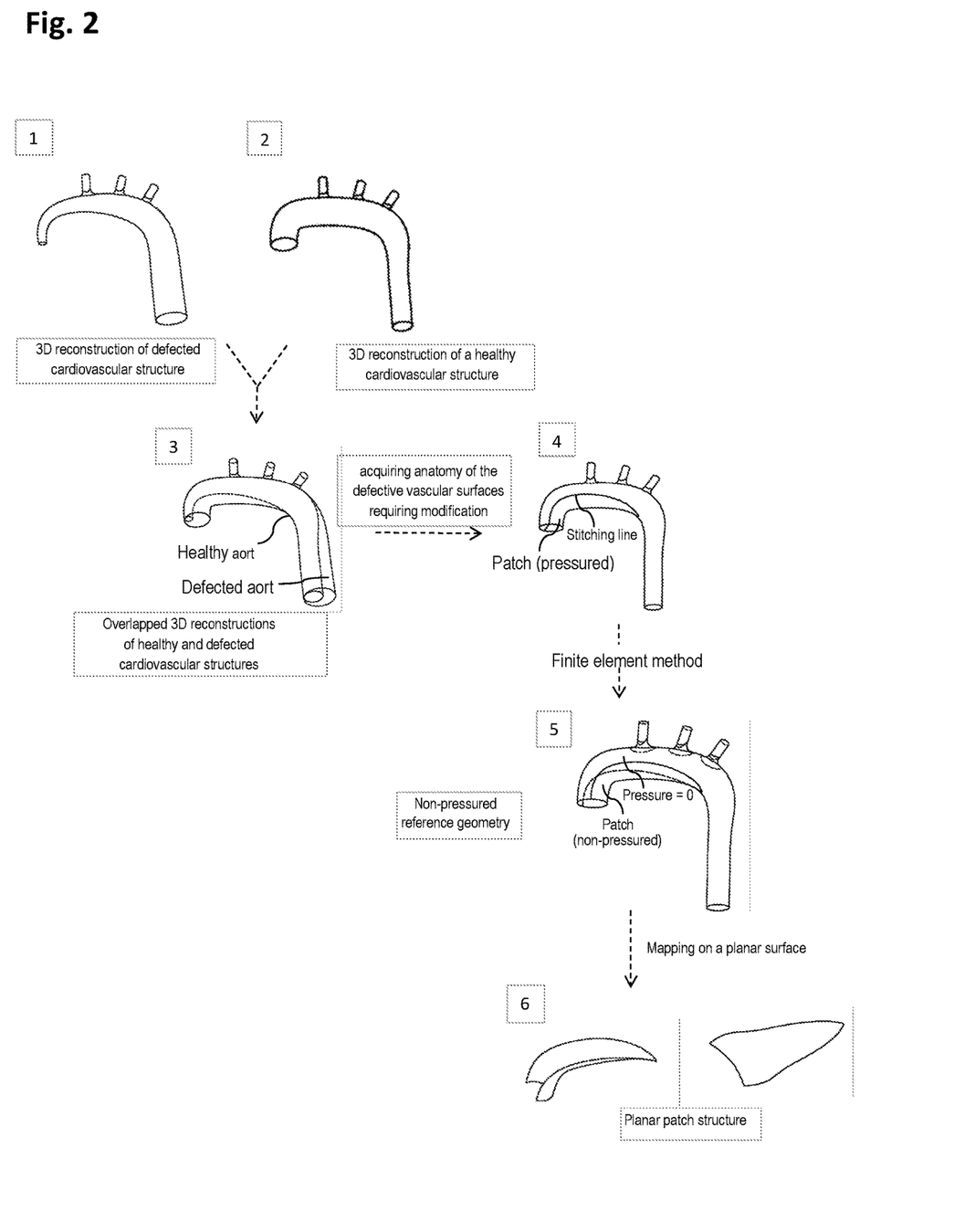
FIG. 2 demonstrates a series of schematic views of healthy and defective vascular anatomies representing operational steps of a system that includes a pre-operative patch generation device.
Figure 3:
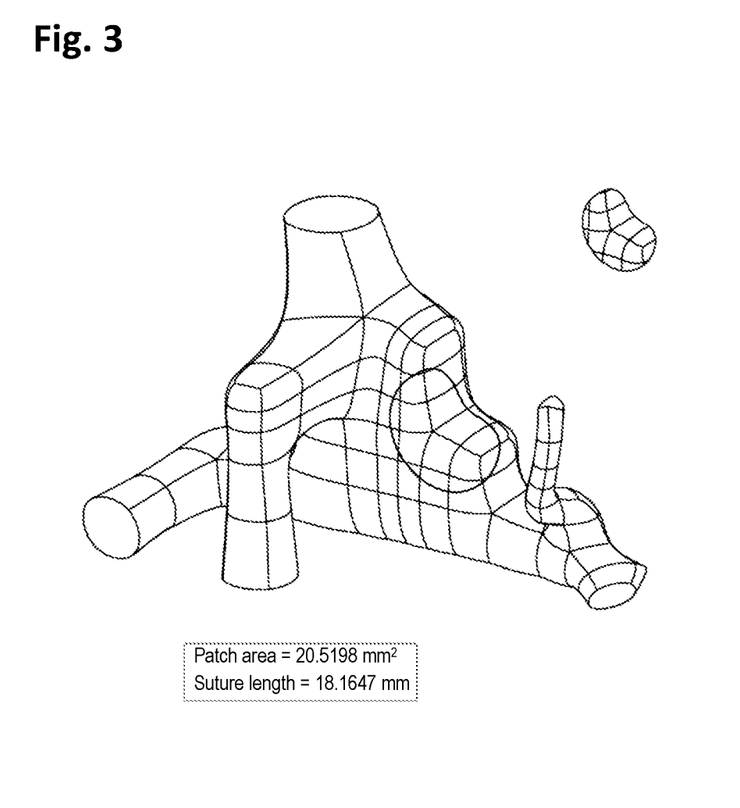
FIG. 3 is an example illustrating three-dimensional patient specific vascular graft structures.

The following numerals are referred to in the detailed description of the present disclosure:
1) Patch generation device
2) Modelling module
3) Integration module
4) Transformation module
5) Prototype module With reference to FIGS. 1-3, the present disclosure relates to a system for manufacturing of vascular patches in the form pre-operative surgical planning prototypes providing optimized patient specific 3-D patch geometries.

Congenital cardiovascular defects in neonatal and pediatric patients are treated through palliative reconstructive surgical operations where the commercially available artificial vascular transplants/grafts fabricated from synthetic materials are implanted. Since patient-specific cardiovascular anatomies are highly complex and cardiovascular structures of neonatal and pediatric patients grow in size while their vascular micro-structure alters significantly with aging under increasing mechanical loads, artificial grafts not having specifically engineered geometries are unable to comply with changing vascular size and fail beyond their operating dimensions unlike live tissue.

The vascular grafts are generally fabricated from synthetic materials. Biocompatible and blood compatible artificial grafts replaceable with the defected tissue are required for the treatment of neonatal and pediatric cardiovascular defects. To this end, suitable polymeric vascular structures are implanted to treat cardiovascular defects of pediatric or neonatal patients. Vascular conduits and patches conventionally used for this purpose can be referred to as for instance Polyethylene terephthalate, Polytetrafluoroethylene, bovine or swine pericardium (Lam et al., 2012; Kapadia et al., 2008: Laube et al., 2000; Hoshi et al., 2013: Pok and Jacot, 2011).

Autogenic pericardial implants are ideal for the neonatal and pediatric patients due to their capability of regeneration and complying with the growth of the patient. The essential function needed to be fulfilled by various artificial grafts is the biological and mechanical compatibility with the patient's tissue. In this regard, polyurethanes having structural diversity are considered as one of the most biocompatible materials usable as of today.

The present disclosure proposes a system that includes a patch generation device (1) for the structuring of patient-specific cardiovascular grafts as a computer-aided system producing planar and 3D graft prototypes to serve as a reference prototype during the pre-operative form giving stage of a patch graft by the surgeon, the patch graft given shape as such being than implanted to the defected part of the patient's cardiovascular vessels. Therefore, the present disclosure proposes fabrication of specially configured reference graft prototypes having patient-specific geometries.

The planning of the patient specific graft is based on MRI or CT scanning of the patient's vascular anatomy by which 3D hemodynamic reconstruction of the vascular structures are performed. For instance, computer software modules by the commercial names 3D DOCTOR, MIMICS or SCAN-IP running on the patch generation device (1) can be used in this regard. The anatomic reconstruction is performed by the patch generation device's (1) processing unit with multi-color differentiation according to hemodynamic differences within the cardiovascular structure.

The patient's reconstructed cardiovascular anatomy is integrated with the ideal healthy 3D cardiovascular anatomy construction by the patch generation device (1), preferably using an appropriate software module such as for instance SketchCad™ so as to determine the specific parts of the vascular structure to which a patch graft being restructured in a patient-specific manner can be implanted on the patient's vascular structure. The integration of the healthy and defected vascular structures is effectuated through conformal mapping technique by which the two anatomies are juxtaposed while the defective vascular surfaces requiring modification are indicated on an image display medium in communication with the patch generation device (1) with a distinguishing color in comparison to the ideal vascular surface.

It is to be noted that the acquired anatomy of the defective vascular surfaces requiring modification therefore represents the graft structure with a specific vascular geometry obtained with the blood pressure therein, i.e. in post-operative state. To obtain the pre-operative vascular anatomy of the graft geometry in non-pressured state, finite element method is used to eliminate the pressure effect on the geometrical structure of the defective vascular surfaces and the acquired corresponding graft structure. The pressure effect is removed by finite element method so that the acquired graft structure is geometrically reshaped, typically reduced in size in a hemodynamically location-specific proportionality so as to be able to take its post-operative shape when the pressure effect will be present. Preferably, an appropriate software module such as Adina™ can be used in this procedure.

Subsequently, the unpressurised state graft structure is mapped on a planar surface providing a master structure as a reference geometry for the patch graft to be cut by the surgeon in order for implanting to the pediatric or neonatal patient replacing the defective cardiovascular graft.

The patch generation device (1) according to the present disclosure effectuates planar and 3-D printing of the patient-specific graft geometries as prototypes so as to be used by the surgeon as a reference structure when cutting the artificial biocompatible patch to be implanted, thereby manifestly demonstrating the 3-D geometry of the artificial graft to replace the patient's defective vascular graft. While the planar patch prototype will serve for cutting the patch material along predetermined cutting lines in a specific size, the 3-D patch prototype will serve as a 3-D model corresponding to the 3-D geometry of the artificial graft required to be implanted. Therefore, the graft prototypes fabricated according to the proposed system serve to the purpose of assisting the surgeon in implanting the patch graft in an accurately positioned manner so that undesired post-operative graft deformations in treatment of congenital cardiovascular defects in neonatal and pediatric patients can be eliminated.

The system that includes the patch generation device (1) according to the present disclosure is a computer-aided system including hardware in the form of at least one memory 6 and at least one processor 7 having circuitry that is executable to run a plurality of software modules stored in memory 6 for effectuating generation of patient-specific graft geometries. A modeling module (2) is executable to perform hemodynamic reconstruction of the patient's vascular structures so as to perform multicolor demonstration of the hemodynamic behavior in the patient's vascular structures. The reconstruction task includes formation and scaling of the vascular anatomy so as to be processed by execution of an integration module (3) as will be delineated below.

The integration module (3) is executable to perform formation and scaling of a healthy vascular anatomy with which the patient's reconstructed cardiovascular anatomy is integrated in the manner that said reconstructed defected vascular anatomy and the healthy vascular anatomy are overlapped to reveal the patient's specific anatomical parts into which a patch graft implantation is needed.

The formation and scaling of the patient's vascular anatomy by execution of the modelling module (2) and a healthy vascular anatomy by execution of the integration module (3) enables the integration module (3) to isolate and geometrically specify the exact surface area and associated stitching lines on the patient's vascular anatomy by combining both of the two three-dimensional anatomies of healthy and defective vascular structures.

Further, a transformation module (4), is executable to convert the obtained patch graft shape on the surface of the defected vascular structure under the effect of blood pressure to a non-pressured vascular structure by finite element method allowing reconstruction of a 3-D patch graft model in pre-operative state. The transformation module (4) is executable to also effectuate mapping of the patch graft geometry on a plane surface.

According to the present disclosure, a prototype module (5) is then executable to print the pre-operative state three-dimensional patch graft model as well as the planar patch graft in the form of planar and three-dimensional objects. The planar object can be used by the surgeon for cutting the artificial patch graft by surgical scissors in a form specifically adapted to the patient. Further, the surgeon will be provided with a patient-specific 3-D model of the graft patch to enable him acquire a 3-D geometry replica of the artificial graft required to be implanted.

The patch geometry will enable the surgeon to detect graft positions that may lead to undesired graft deformation such as wrinkling or to optimize stitching to remove the possibility of excessive stitching that impose unnecessary loads on the graft.

It is to be noted that the reconstruction of a 3-D patch graft model according to the present disclosure is also applicable to the great arteries including pulmonary artery, pulmonary veins and aorta.

3-D printing techniques have recently become extensively known to the skilled worker. It is also worthy of note that 3-D printing equipment is commercially available in the market. 3-D printing techniques particularly differ in the manner layers of the final object are built one above another. Use of melting or softening material as well as selective laser sintering (SLS), fused deposition modeling (FDM) and stereolithography (SLA) constitute the common technologies.

In a nutshell, the present disclosure proposes a system that includes a patch generation device (1) for manufacturing of vascular patches in the form of pre-operative surgical planning prototypes providing optimized patient-specific patch geometries, said patch generation device (1) comprising a processing unit effectuating processing of the optimized patient-specific patch geometries.

In one embodiment, said patch generation device (1) comprises a modeling module (2) executable to perform structural and hemodynamic reconstruction of a patient's vascular structures.

In a further embodiment, said patch generation device (1) comprises an integration module (3) executable to perform formation and scaling of a healthy vascular anatomy with which the patient's reconstructed cardiovascular anatomy is integrated in the manner that said reconstructed defected vascular anatomy and the healthy vascular anatomy are overlapped to reveal the patient's specific anatomical parts into which a patch graft implantation is envisageable.

In a further embodiment of the present disclosure, said patch generation device (1) comprises a transformation module (4), executable to convert the revealed patient-specific anatomical parts under the effect of simulated blood pressure and into which a patch graft implantation is envisageable to a non-pressured vascular structure by finite element method allowing reconstruction of a 3-D patch graft model in pre-operative state.

In a further embodiment of the present disclosure, said modeling module (2) executable to perform formation and scaling of the patient's vascular anatomy enabling multicolor demonstration of the hemodynamic behavior and performance in the patient's vascular structures.

In a further embodiment of the present disclosure, said integration module (3) executable to isolate and geometrically specify an exact surface loading and associated stitching forces on the patient's vascular anatomy by combining both of the three-dimensional anatomies of the healthy and defected vascular anatomies.

In a further embodiment of the present disclosure, said transformation module (4) executable to effectuate mapping of the surface loading and stitching forces on a plane surface generating a planar reconstruction of pre-operative state patch graft model with predetermined cutting lines in a specific geometry providing a master structure as a reference geometry.

In a further embodiment of the present disclosure, a prototype module (5) of the patch generation device (1) executable to print the reconstructed pre-operative state three-dimensional patch graft model as a surgical template.

In a further embodiment of the present disclosure, a prototype module (5) of the patch generation device (1) executable to print the reconstructed pre-operative state planar patch graft model.

In a further embodiment of the present disclosure, said modeling module (2) executable to perform formation and scaling of the patient's vascular anatomy based on MRI or CT scans by which 3D hemodynamic reconstruction of the vascular structures is performed.

In a further embodiment of the present disclosure, integration of the healthy and defected vascular anatomies is effectuated through a computational technique such as conformal mapping technique.

In a further embodiment of the present disclosure, the transformation module (4) executable to effectuate conversion of the revealed post-operative state patient-specific anatomical parts into which a patch graft implantation is envisageable to generate a pre-operative state three-dimensional patch graft model in non-pressured state such that finite element method is used to eliminate the pressure effect on the pre-operative state three-dimensional patch graft model.

In a further embodiment of the present disclosure, the pre-operative state three-dimensional patch graft model in non-pressured state is reduced in size in a hemodynamically location-specific proportionality so as to be able to take its post-operative shape when the pressure effect will be present.

In a further embodiment of the present disclosure, said patch graft model is additionally dimensionally restructured in a patient specific manner based on specific predetermined classifications from a patient database according to the demographic data of the patient. In other words, the final structure of the patch graft model can undergo a second transformation only to adapt the same to the specific anatomical conditions of the patient, such specific anatomical conditions including demographic properties such as for instance age, sex and weight of the patient. It is to be noted that a specific database containing such demographic data can be used to reveal characteristic differences between patients regarding the structural effects on the patch grafts in terms of the surface loading and stitching forces. As a specific example, patch grafts of two otherwise identical patients to be applied under identical anatomical conditions can be structurally slightly different depending on the weight of each patient.

The present disclosure further proposes a method for fabricating vascular patches in the form pre-operative surgical planning prototypes providing optimized patient-specific patch geometries by means of a patch generation device (1), said method comprising the steps of, a) performing structural and hemodynamic reconstruction of a patient's vascular structures by a modeling module (2), b) performing formation and scaling of a healthy vascular anatomy with which the patient's reconstructed cardiovascular anatomy is integrated by an integration module (3) in the manner that said reconstructed defected vascular anatomy and the healthy vascular anatomy are overlapped to reveal the patient's specific anatomical parts into which a patch graft implantation is envisageable, c) converting by a transformation module (4) the revealed patient-specific anatomical parts under the effect of blood pressure and into which a patch graft implantation is envisageable to a non-pressured vascular structure by finite element method allowing reconstruction of a 3-D patch graft model in pre-operative state and, d) printing the reconstructed pre-operative state three-dimensional patch graft model.

In a further embodiment of the present disclosure, said method further comprises the step of mapping of the surface area and associated stitching lines on a plane surface generating a planar reconstruction of pre-operative state patch graft model with predetermined cutting lines in a specific geometry by said transformation module (4).

In a further embodiment of the present disclosure, said method further comprises the step of printing the reconstructed pre-operative state planar patch graft model.

The present disclosure further proposes a pre-operative state patch graft model manufactured according to the method for fabricating vascular patches in the form pre-operative surgical planning prototypes.

In a further embodiment of the present disclosure, a pre-operative state patch graft model manufactured by said patch generation device is proposed.

The present disclosure further proposes a conduit manufactured by said patch generation device, wherein said conduit is manufactured in the form of a tubular 3D rapid prototype.

In sum, the determination of the physical characteristics and the optimum geometrical shape of the artificial patch including the stitching line's length and geometry is made by the surgeon during the surgical operation. Two-dimensional standard artificial patch materials in rectangular form are needed to be cut in appropriate sizes according to the specific needs of the patient. Otherwise an inappropriately structured patch may cause graft deformations if not tailored to the individual patient's anatomy, additionally causing stress on the stitches, consumption of extra energy by the heart and deformations due to the deviation of the hemodynamic forces on the vascular cells from the physiological values.

Therefore, the patient-specific models/prototypes of graft patches play a crucial role in assisting the surgeon while he designs the structural aspects of the artificial patch. It is also further critical that this process of design should be terminated in the quickest manner as possible because the time period the surgeon needs during the surgery for designing the artificial patch may cause brain and systemic tissue damage in neonatal and pediatric patients. To this end, patient-specific models/prototypes of graft patches in accordance with the present disclosure substantially accelerate the in-surgery procedures carried out by the surgeon.

The subject-matter of the disclosure may also relate, among others, to the following aspects:

1. A patch generation device (1) for generation of vascular patches in the form of pre-operative surgical planning models providing optimized patient-specific patch geometries, said patch generation device (1) comprising a processing unit effectuating processing of the optimized patient-specific patch geometries characterized in that;
said patch generation device (1) comprises a modeling module (2) performing structural and hemodynamic reconstruction of a patient's vascular structures, said patch generation device (1) comprises an integration module (3) performing formation and scaling of a healthy vascular anatomy with which the patient's reconstructed cardiovascular anatomy is integrated in the manner that said reconstructed defected vascular anatomy and the healthy vascular anatomy are overlapped to reveal the patient's specific anatomical parts into which a patch graft implantation is envisageable, said patch generation device (1) comprises a transformation module (4), converting the revealed patient-specific anatomical parts under the effect of blood pressure and into which a patch graft implantation is envisageable to a non-pressured vascular structure by finite element method whereby construction of a 3-D patch graft model in pre-operative state is facilitated and, said integration module (3) isolates and geometrically specifies an exact surface loading and associated stitching forces on the patient's vascular anatomy by combining both of the three-dimensional anatomies of the healthy and defected vascular anatomies.

2. A patch generation device (1) as set forth in Aspect 1, characterized in that said modeling module (2) performs formation and scaling of the patient's vascular anatomy enabling multicolor demonstration of the hemodynamic behavior and performance in the patient's vascular structures.

3. A patch generation device (1) as set forth in Aspect 1, characterized in that said transformation module (4) effectuates mapping of the surface loading and stitching forces on a plane surface generating a planar reconstruction of pre-operative state patch graft model with predetermined cutting lines in a specific geometry providing a master structure as a reference geometry.

4. A patch generation device (1) as set forth in Aspect 1, characterized in that a prototype module (5) of the patch generation device (1) prints the reconstructed pre-operative state three-dimensional patch graft model as a template.

5. A patch generation device (1) as set forth in Aspect 3, characterized in that a prototype module (5) of the patch generation device (1) prints the reconstructed pre-operative state planar patch graft model.

6. A patch generation device (1) as set forth in Aspect 2, characterized in that said modeling module (2) performs formation and scaling of the patient's vascular anatomy based on MRI or CT scans by which 3D hemodynamic reconstruction of the vascular structures is performed.

7. A patch generation device (1) as set forth in Aspect 1, characterized in that integration of the healthy and defected vascular anatomies is effectuated through a computational technique.

8. A patch generation device (1) as set forth in Aspect 1, characterized in that the transformation module (4) effectuates conversion of the revealed post-operative state patient-specific anatomical parts into which a patch graft implantation is envisageable to generate a pre-operative state three-dimensional patch graft model in non-pressured state such that finite element method is used to eliminate the pressure effect on the pre-operative state three-dimensional patch graft model.

9. A patch generation device (1) as set forth in Aspect 8, characterized in that the pre-operative state three-dimensional patch graft model in non-pressured state is reduced in size in a hemodynamically location-specific proportionality so as to be able to take its post-operative shape when the pressure effect will be present.

10. A patch generation device (1) as set forth in Aspect 1 or 3, characterized in that said patch graft model is additionally dimensionally restructured in a patient specific manner based on specific predetermined classifications from a patient database according to the demographic data of the patient.

11. A method for fabricating vascular patches in the form pre-operative surgical planning prototypes providing optimized patient-specific patch geometries by means of a patch generation device (1) as set forth in Aspect 1, said method comprising the steps of;

a) performing structural and hemodynamic reconstruction of a patient's vascular structures by a modeling module (2), b) performing formation and scaling of a healthy vascular anatomy with which the patient's reconstructed cardiovascular anatomy is integrated by an integration module (3) in the manner that said reconstructed defected vascular anatomy and the healthy vascular anatomy are overlapped to reveal the patient's specific anatomical parts into which a patch graft implantation is envisageable, c) converting by a transformation module (4) the revealed patient-specific anatomical parts under the effect of blood pressure and into which a patch graft implantation is envisageable to a non-pressured vascular structure by finite element method whereby construction of a 3-D patch graft model in pre-operative state is facilitated and, d) isolating and geometrically specifying by an integration module (3) an exact surface loading and associated stitching forces on the patient's vascular anatomy by combining both of the three-dimensional anatomies of the healthy and defected vascular anatomies.

e) printing the reconstructed pre-operative state three-dimensional patch graft model.

12. A method for fabricating vascular patches in the form pre-operative surgical planning prototypes as set forth in Aspect 11, said method further comprises the step of mapping of the surface area and associated stitching lines on a plane surface generating a planar reconstruction of pre-operative state patch graft model with predetermined cutting lines in a specific geometry by said transformation module (4).

13. A method for fabricating vascular patches in the form pre-operative surgical planning prototypes as set forth in Aspect 12, said method further comprises the step of printing the reconstructed pre-operative state planar patch graft model.

14. A pre-operative state patch graft model generated by the patch generation device (1) according to Aspect 1.

15. A conduit manufactured by the patch generation device (1) according to Aspect 4, wherein said conduit is manufactured in the form of a tubular 3D rapid prototype.

Each component described herein may include additional, different, or fewer components. For example, the processor may be multiple processors, the memory may be multiple memories, and the each of the modules may be multiple modules. In addition, the functionality of the system may be implemented with additional, different, or fewer components. In addition, the operations of the system described and illustrated herein, may be performed in a different order. Also, modules as described herein include a combination of hardware, such as circuitry, and software that is executable to provide the described functionality.

The methods, devices, modules, processing, circuitry, and logic described above may be implemented in many different ways and in many different combinations of hardware and software. For example, all or parts of the implementations may be circuitry that includes an instruction processor, such as a Central Processing Unit (CPU), microcontroller, or a microprocessor; or as an Application Specific Integrated Circuit (ASIC), Programmable Logic Device (PLD), or Field Programmable Gate Array (FPGA); or as circuitry that includes discrete logic or other circuit components, including analog circuit components, digital circuit components or both; or any combination thereof. The circuitry may include discrete interconnected hardware components or may be combined on a single integrated circuit die, distributed among multiple integrated circuit dies, or implemented in a Multiple Chip Module (MCM) of multiple integrated circuit dies in a common package, as examples.

Accordingly, the circuitry may store or access instructions for execution, or may implement its functionality in hardware alone. The instructions may be stored in a tangible storage medium that is other than a transitory signal, such as a flash memory, a Random Access Memory (RAM), a Read Only Memory (ROM), an Erasable Programmable Read Only Memory (EPROM); or on a magnetic or optical disc, such as a Compact Disc Read Only Memory (CDROM), Hard Disk Drive (HDD), or other magnetic or optical disk; or in or on another machine-readable medium. A product, such as a computer program product, may include a storage medium and instructions stored in or on the medium, and the instructions when executed by the circuitry in a device may cause the device to implement any of the processing described above or illustrated in the drawings.

The implementations may be distributed. For instance, the circuitry may include multiple distinct system components, such as multiple processors and memories, and may span multiple distributed processing systems. Parameters, databases, and other data structures may be separately stored and managed, may be incorporated into a single memory or database, may be logically and physically organized in many different ways, and may be implemented in many different ways. Example implementations include linked lists, program variables, hash tables, arrays, records (e.g., database records), objects, and implicit storage mechanisms. Instructions may form parts (e.g., subroutines or other code sections) of a single program, may form multiple separate programs, may be distributed across multiple memories and processors, and may be implemented in many different ways. Example implementations include stand-alone programs, and as part of a library, such as a shared library like a Dynamic Link Library (DLL). The library, for example, may contain shared data and one or more shared programs that include instructions that perform any of the processing described above or illustrated in the drawings, when executed by the circuitry.

To clarify the use of and to hereby provide notice to the public, the phrases "at least one of <A>, <B>, . . . and <N>" or "at least one of <A>, <B>, . . . <N>, or combinations thereof" or "<A>, <B>, . . . and/or <N>" are defined by the Applicant in the broadest sense, superseding any other implied definitions hereinbefore or hereinafter unless expressly asserted by the Applicant to the contrary, to mean one or more elements selected from the group comprising A, B, . . . and N. In other words, the phrases mean any combination of one or more of the elements A, B, . . . or N including any one element alone or the one element in combination with one or more of the other elements which may also include, in combination, additional elements not listed. In addition, the use of the article "a" in the claims is equivalent to "one or more."

While various embodiments have been described, it will be apparent to those of ordinary skill in the art that many more embodiments and implementations are possible. Accordingly, the embodiments described herein are examples, not the only possible embodiments and implementations.

The invention claimed is:

1. A patch generation device comprising:
a processor configured to effectuate processing of optimized patient-specific patch geometries by generation of vascular patches in the form of pre-operative surgical planning models to provide the optimized patient-specific patch geometries;
a modeling module executed by the processor to perform structural and hemodynamic reconstruction of vascular anatomy of a patient to generate a reconstructed cardiovascular anatomy of the patient;
an integration module executable by the processor to perform formation and scaling of a healthy vascular anatomy with which the reconstructed cardiovascular anatomy of the patient is integrated in a manner that a defected vascular anatomy included in the reconstructed cardiovascular anatomy and the healthy vascular anatomy are overlapped to reveal patient-specific anatomical parts of the vascular anatomy of the patient into which a patch graft implantation is envisageable,
a transformation module executed by the processor to convert the revealed patient-specific anatomical parts, under the simulated effect of blood pressure and into which the patch graft implantation is envisageable, to a non-pressured vascular structure by finite element method;
said transformation module further executed by the processor to generate a three-dimensional patch graft model in pre-operative state; and,
said integration module further executable by the processor to isolate and geometrically specify a surface loading and associated stitching forces on the vascular anatomy of the patient by combination of the healthy vascular anatomy and the defected vascular anatomy in the three-dimensional-dimensional patch graft model.

2. The patch generation device as set forth in claim 1, wherein said modeling module is executed by the processor to perform formation and scaling of the vascular anatomy of the patient to generate a visual display of a multicolor demonstration of the hemodynamic behavior and performance in vascular structures within the vascular anatomy of the patient.

3. The patch generation device as set forth in claim 2, wherein said modeling module is executed by the processor to perform formation and scaling of the vascular anatomy of the patient based on magnetic resonance imaging (MRI) or computed tomography (CT) scans by which three-dimensional hemodynamic reconstruction of vascular structures included in the vascular anatomy of the patient is performed.

4. The patch generation device as set forth in claim 1, wherein said transformation module is executed by the processor to effectuate computer-based mapping of the surface loading and stitching forces on a plane surface by generation of a planar reconstruction of a pre-operative state of the three-dimensional patch graft model with predetermined cutting lines in a specific geometry to provide a master structure as a reference geometry.

5. The patch generation device as set forth in claim 4, wherein the prototype module is further executed by the processor to cause the planar reconstruction of the pre-operative state of the three-dimensional patch graft model to print.

6. The patch generation device as set forth in claim 1, further comprising a prototype module executable by the processor to cause the three-dimensional patch graft model to print as a template in a reconstructed pre-operative state.

7. The patch generation device as set forth in claim 6, wherein a printout of the template in the reconstructed pre-operative state is a conduit manufactured by the patch generation device, wherein said conduit is manufactured in the form of a tubular three-dimensional rapid prototype.

8. The patch generation device as set forth in claim 1, wherein integration of the healthy vascular anatomy and the defected vascular anatomy is effectuated through a computational technique.

9. The patch generation device as set forth in claim 1, wherein the transformation module is executed by the processor to effectuate conversion of revealed post-operative state patient-specific anatomical parts into which the patch graft implantation is envisageable to generate the pre-operative state of the three-dimensional patch graft model in a non-pressured state such that a finite element method is used to eliminate a pressure effect on the pre-operative state of the three-dimensional patch graft model.

10. The patch generation device as set forth in claim 9, wherein the pre-operative state of the three-dimensional patch graft model in the non-pressured state is reduced in size in a hemodynamically location-specific proportionality so as to be able to take its post-operative shape when the pressure effect is present.

11. The patch generation device as set forth in claim 1, said three-dimensional patch graft model is additionally dimensionally restructured in a patient specific manner based on specific predetermined classifications retrieved from a patient database according to demographic data of the patient.

12. The patch generation device as set forth in claim 1, further comprising a pre-operative state patch graft model generated by the patch generation device.

13. A method for fabricating vascular patches in the form pre-operative surgical planning prototypes providing optimized patient-specific patch geometries by means of a patch generation device, said method comprising the steps of;

performing computer based structural and hemodynamic reconstruction of a vascular anatomy of a patient by modeling with the patch generation device to generate a reconstructed cardiovascular anatomy of the patient that includes a defected vascular anatomy, performing computer based formation and scaling of a healthy vascular anatomy with which the reconstructed cardiovascular anatomy of the patient is integrated in a manner that said defected vascular anatomy and said healthy vascular anatomy are overlapped to reveal specific anatomical parts of the vascular anatomy of the patient into which a patch graft implantation is envisageable, converting the revealed specific anatomical parts of the patient, under the simulated effect of blood pressure and into which a patch graft implantation is envisageable, to a non-pressured vascular structure by a computer based finite element method;

constructing a computer based three-dimensional patch graft model in pre-operative state;

isolating and geometrically specifying a surface loading and associated stitching forces on the vascular anatomy of the patient by combining the healthy vascular anatomy and the defected vascular anatomy in the three-dimensional patch graft model; and printing the three-dimensional patch graft model.

14. The method for fabricating vascular patches in the form pre-operative surgical planning prototypes as set forth in claim 13, said method further comprises: performing computer-based mapping of a surface area and associated stitching lines on a plane surface; generating a computer-based planar reconstruction of pre-operative state of the three-dimensional patch graft model with predetermined cutting lines in a specific geometry.

15. The method for fabricating vascular patches in the form pre-operative surgical planning prototypes as set forth in claim 14, said method further comprises the step of printing the computer-based planar reconstruction of pre-operative state of the three-dimensional patch graft model.

* * * * *